US00PP32488P2

(12) United States Plant Patent
Holtmaat

(10) Patent No.: US PP32,488 P2
(45) Date of Patent: Nov. 17, 2020

(54) ***RUDBECKIA* PLANT NAMED 'RUDPA297'**

(50) Latin Name: *Rudbeckia hirta*
Varietal Denomination: RUDPA297

(71) Applicant: Henricus Maria Joseph Holtmaat, Zuidwolde (NL)

(72) Inventor: Henricus Maria Joseph Holtmaat, Zuidwolde (NL)

(73) Assignee: NOVA PERENNE BV, Zuidwolde (NL)

( * ) Notice: Subject to any disclaimer, the term of this patent is extended or adjusted under 35 U.S.C. 154(b) by 0 days.

(21) Appl. No.: 16/873,154

(22) Filed: Feb. 15, 2020

(30) Foreign Application Priority Data

Jan. 24, 2020 (QZ) ..... PBR 2020/0007

(51) Int. Cl.
*A01H 5/02* (2018.01)
*A01H 6/14* (2018.01)

(52) U.S. Cl.
USPC ..... Plt./474

(58) Field of Classification Search
USPC ..... Plt./263.1, 474
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Rudbeckia* plant named 'RUDPA297' that is characterized by its vigorous growth habit yet maintaining a compact plant habit, its very floriferous blooming habit, and its inflorescences with disks that are green-yellow in color and ray florets that are yellow-orange in color.

2 Drawing Sheets

Botanical classification: *Rudbeckia hirta.*
Variety denomination: 'RUDPA297'.

CROSS REFERENCE TO RELATED APPLICATIONS

This application is related to U.S. Plant Patent Applications filed for plants derived from the same breeding program that are entitled *Rudbeckia* Plant Named 'RUDHT37' (U.S. Plant Pat. No. 30,657) and *Rudbeckia* Plant Named 'RUDHT25' (U.S. Plant Pat. No. 30,728). This application claims priority to European Community Plant Variety Office (CPVO) Plant Breeder's Rights Application No. 2020/0007 filed on Jan. 6, 2020 under 35 U.S.C. 119(f), the entire contents of which is incorporated by reference herein.

BACKGROUND OF THE INVENTION

The present invention relates to a new and distinct cultivar of *Rudbeckia hirta* and will hereafter by referred to by its cultivar name, 'RUDPA297'. The new cultivar is an herbaceous perennial grown for use as a landscape plant.

'RUDPA297' was derived from a breeding program conducted by the Inventor at a nursery in Zuidwolde, The Netherlands. The objective of the breeding program was to select new cultivars of *Rudbeckia* with floriferous blooming habits and compact plant habits.

'RUDPA297' was selected in July of 2018 by the Inventor from amongst seedlings in a trial field that had been planted with seed derived from open pollination of numerous unpatented and unnamed proprietary plants from the Inventor's breeding program in July of 2017. The exact parentage is therefore unknown.

Asexual propagation of the new cultivar was first accomplished under the direction of the Inventor by tissue culture using meristematic tissue in Heerhugowaard, The Netherlands in March of 2019. Asexual propagation by tissue culture has determined that the characteristics of the new cultivar are stable and are reproduced true to type in successive generations.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to a website listing by AB-Cultivars (a company owned by the Inventor).

SUMMARY OF THE INVENTION

The following traits have been repeatedly observed and represent the characteristics of the new cultivar. These attributes in combination distinguish 'RUDPA297' as a unique cultivar of *Rudbeckia.*

1. 'RUDPA297' exhibits a vigorous growth habit yet maintains a compact plant habit.
2. 'RUDPA297' exhibits a very floriferous blooming habit.
3. 'RUDPA297' exhibits inflorescences with disks that are green-yellow in color and ray florets that are yellow-orange in color.

'RUDPA297' can be compared to the *Rudbeckia* cultivars 'RUDHT37' and 'RUDHT25'. 'RUDHT37' is similar to 'RUDPA297' in ray floret color. 'RUDHT37' differs from 'RUDPA297' in being taller in height, in having a less spreading plant habit, in commencing bloom later in the flowering season, and in having inflorescence disk florets that are dark brown in color. 'RUDHT25' is similar to 'RUDPA297' in foliage color. 'RUDHT25' differs from 'RUDPA297' in having a shorter plant height and inflorescences that open later in the season, are smaller in diameter with ray florets that are yellow-orange in color with grey-purple to brown bases.

BRIEF DESCRIPTION OF THE DRAWINGS

The accompanying colored photographs illustrate the overall appearance and distinct characteristics of the new *Rudbeckia*. The photographs were taken of a 6-month-old plant of 'RUDPA297' as grown outdoors in a 17-cm container in Zuidwolde, The Netherlands.

The photograph in FIG. 1 is a side view of 'RUDPA297' in bloom.

Figure 1:
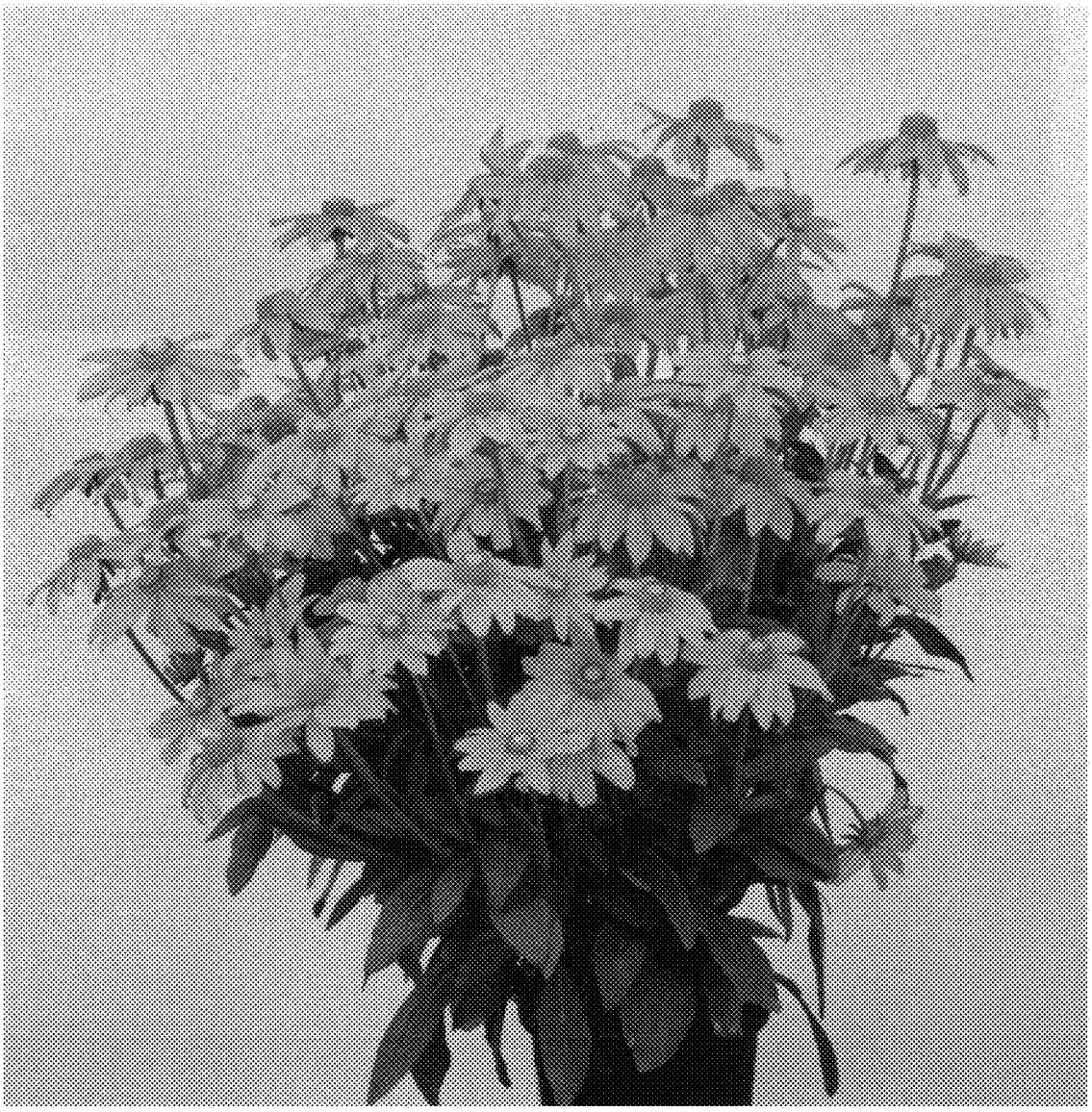
Figure 2:
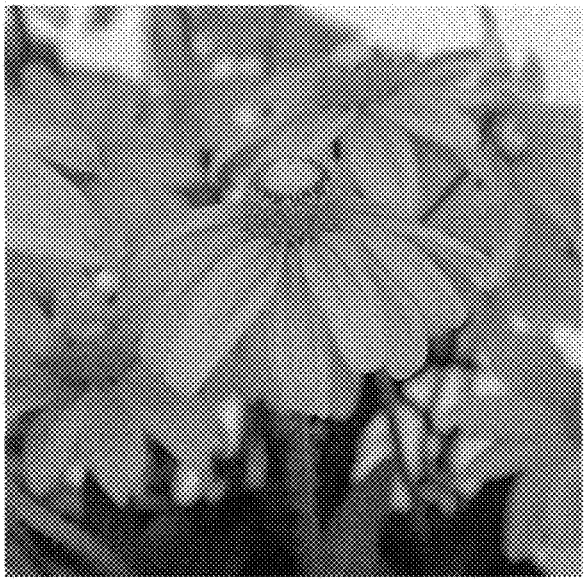

The photograph in FIG. 2 provides a close-up view of an inflorescence of 'RUDPA297'.

Figure 3:
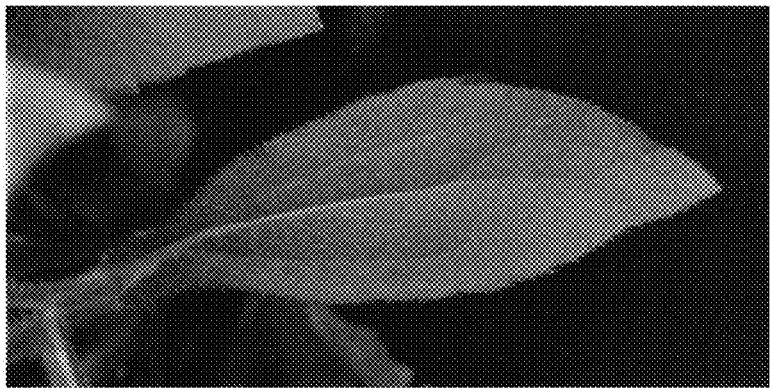

The photograph in FIG. 3 provides a close-up view of the foliage of 'RUDPA297'.

The colors in the photographs are as close as possible with the photographic and printing technology utilized and the color values cited in the detailed botanical description accurately describe the colors of the new *Rudbeckia*.

BOTANICAL DESCRIPTION OF THE PLANT

The following is a detailed description of 6-month-old plants of 'RUDPA297' as grown outdoors in 17-cm containers in Zuidwolde, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Average of 13 weeks from early summer to late summer in The Netherlands.

*Plant type*.—Perennial.

*Plant habit*.—Upright, compact.

*Plant shape*.—Broad obovate.

*Height and spread*.—Average of 47 cm in height from soil level to top of foliar plane and 63 cm in height from soil level to top of floral plane, 72.3 cm in diameter.

*Hardiness*.—At least in U.S.D.A. Zones 4 to 10.

*Diseases and pests*.—No susceptibility and resistance to diseases or pests has been observed.

*Root description*.—Fine and fibrous.

*Propagation*.—Tissue culture.

*Root development*.—An average of 3 weeks for root initiation with a young rooted plant produced in an average of 6 weeks.

*Growth rate and vigor*.—Vigorous yet compact.

Stem description:

*Stem shape*.—Slightly angled.

*Stem color*.—Young stems; 144A, mature stems; 144B, axially striped 144A.

*Stem size*.—An average of 5 mm in diameter and an average of 23 cm in length.

*Stem surface*.—Moderately glossy and densely covered with strigose hairs an average of 2 mm in length and close to NN155D in color.

*Stem number*.—Average of 12 main stems, 7 lateral branches per main stem.

*Internode length*.—An average of 3.1 cm in length.

*Stem aspect*.—Main stems an average angle of 17.5° to vertical, lateral branches in an average angle of 25° to main stems.

*Branching*.—Freely branching from base with lateral stems, strong branches.

Foliage description:

*Leaf shape*.—Narrow obovate.

*Leaf division*.—Simple.

*Leaf base*.—Long cuneate.

*Leaf apex*.—Bluntly acute.

*Leaf venation*.—Pinnate, color upper surface 148C, color lower surface 146C.

*Leaf margins*.—Un-deeply coarsely serrate.

*Leaf attachment*.—Petiolate.

*Leaf arrangement*.—Alternate.

*Leaf size*.—Average of 13 cm in length and 4.7 cm in width.

*Leaf color*.—Young upper and lower surface; 138A, mature upper surface; 137B, mature lower surface; 147B.

*Leaf surface*.—Both surfaces matte, rough to touch, both surfaces densely pubescent with short strigose hairs; an average of 1.5 mm in length and 156D in color.

*Petioles*.—Average of 5 mm in length, 3 mm in diameter, both surfaces slightly glossy and densely covered with strigose hairs, average of 1.5 mm in length, NN155D in color, upper surface color 145B, lower surface color 144C.

Flower description:

*Type*.—Terminal capitulum, consisting of ray florets and disk florets.

*Capitulum number*.—1 per stem, up to 140 per plant.

*Lastingness of inflorescence*.—Average of 2 weeks, persistent.

*Capitulum size*.—Matures to about 3.3 cm in height and 7.2 cm in diameter, disk is an average of 2.3 cm in diameter.

*Fragrance*.—None.

*Involucral bracts* (*phyllaries*).—Broadly cuneate base, obtuse apex, narrow oblong in shape, entire margins, average of 24 arranged in two rows, 1.4 cm in length and 3 mm in width, color; upper surface when fully open NN137B, lower surface when fully open 143A, both surfaces and margins matte and densely covered with strigose hairs; an average of 1.5 mm in length and NN155D in color.

*Receptacle*.—Ovate in shape, an average of 1.3 cm in height, 7 mm in diameter, 157B in color.

*Buds*.—Globular in shape, immature ray florets slightly curved inward and pointed upward, up to 2.5 cm in length and 3.8 cm in diameter, color; immature ray florets 151D, upper side of immature involucral bracts NN137B, under side 138B, surface of involucral bracts densely covered with strigose hairs; average length 1.5 mm, NN155D in color, surface of immature ray florets densely covered with adpressed strigose hairs; average of 0.75 mm in length and 4D I color.

*Peduncle*.—Strong, straight on top of main flowering stem, average of 17.1 cm in length and 4.5 mm in diameter, color; 144A, axially striped 143A, surface moderately glossy sand densely covered with short strigose hairs; an average of 1 mm in length and NN155D in color.

*Ray florets*.—Average of 13, rotate around the disk, lanceolate and very slightly carinate in shape, average of 5.4 cm in length and 2.2 cm in width, emarginate to praemorse apex, cuneate base, entire margins, both surfaces are velvety, matte and glabrous, both surfaces moderately covered with very short adpressed strigose hairs, average of 3 mm in length and 15C in color, held near horizontal, color; when opening upper surface; 17A, changing to 17B at the top, when opening lower surface; 14A, when fully open upper surface and veins; 17A, lower half changing to N25D towards the base, when fully open lower surface; 15A, changing to 15B at the tip, veins N144A.

*Disk florets*.—Average of 800, tubular, 20 whorls arranged spirally on a conical receptacle, lower 90% fused into tube, upper 10% free, about 8 mm in length and 3 mm in width, free lobes have entire margins and are curled backwards, both surfaces glabrous and slightly glossy, color; when opening upper and lower surface; top N144A, mid-section and base 150D, when fully open upper and lower surface; top 12B, mid-section and base 157D, spines; none, bracts; 1 per disk floret, soft, flattened, an average of 6 mm in length and 1 mm in diameter, oblanceolate in shape, acute apex, narrow cuneate base, color apex; 145A to 145B, mid-section; 145C to 145D, base 157D.

Reproductive organs:

*Gynoecium*.—Pistil; 1, 7 mm in length, style; 5 mm in length, color; top 2C, base 155C, stigma; cleft, decurrent, 3 mm in diameter, 2B in color, ovary; NN155A in color.

*Androecium*.—Stamens; 5, filaments; 3 mm in length, 158D in color, anther; narrow oblong in shape, 2.5 mm in length, 0.5 mm in width, 200A in color, pollen; moderate in quantity and 17A in color.

*Fruit/seed*.—None observed to date.

It is claimed:

1. A new and distinct cultivar of *Rudbeckia* plant named 'RUDPA297' substantially as herein illustrated and described.

* * * * *